US012697237B1

(12) United States Patent
Burkart et al.

(10) Patent No.: US 12,697,237 B1
(45) Date of Patent: *Aug. 4, 2026

(54) DELIVERY SYSTEMS AND METHODS OF ENDOLUMINAL DELIVERY OF BRANCHED VASCULAR ENDOPROSTHETIC DEVICES

(71) Applicant: W. L. Gore & Associates, Inc., Newark, DE (US)

(72) Inventors: Dustin C. Burkart, Bellemont, AZ (US); Mark Fillinger, Hanover, NH (US); Larry L. Gibbs, Flagstaff, AZ (US); Brandon C. Hedberg, Flagstaff, AZ (US); Jason D. Hemmer, Flagstaff, AZ (US); Timothy E. Johnston, Flagstaff, AZ (US); Levon M. Majure, Flagstaff, AZ (US); Steven W. Nelson, Flagstaff, AZ (US); Jonathan W. Thom, Flagstaff, AZ (US); Daniel J. Westphal, Flagstaff, AZ (US); William Wilkie, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 200 days.

This patent is subject to a terminal disclaimer.

(21) Appl. No.: 18/096,324

(22) Filed: Jan. 12, 2023

Related U.S. Application Data

(63) Continuation of application No. 16/690,388, filed on Nov. 21, 2019, now Pat. No. 11,559,417, which is a
(Continued)

(51) Int. Cl.
    *A61F 2/954*     (2013.01)
    *A61F 2/07*      (2013.01)
    (Continued)

(52) U.S. Cl.
    CPC ................ *A61F 2/954* (2013.01); *A61F 2/07* (2013.01); *A61F 2/966* (2013.01); *A61F 2/9661* (2020.05);
    (Continued)

(58) Field of Classification Search
    CPC .. A61F 2/07; A61F 2/856; A61F 2/954; A61F 2/95; A61F 2/962; A61F 2/966;
    (Continued)

(56) References Cited

U.S. PATENT DOCUMENTS

| 5,591,228 A | 1/1997 | Edoga |
| 6,042,605 A | 3/2000 | Martin et al. |

(Continued)

FOREIGN PATENT DOCUMENTS

| AU | 2013206712 B1 | 11/2013 |
| EP | 2606851 A1 | 6/2013 |

(Continued)

OTHER PUBLICATIONS

Bellandi G., Venturuzzo G. Endovascular Bilateral Evolutive Common Iliac Artery Aneurysm Repair Using a Zenith Branch Graft Through a Combined Femoro-Brachial Approach in a Patient with Previous EVAR. Eur J Vase Endovasc Surg (2910) 40; pp. 596-598.

*Primary Examiner* — Katherine H Schwiker

(57) ABSTRACT

A catheter assembly for delivery of an expandable implant having at least one branch portal, which utilizes a secondary sleeve for releasably constraining a middle portion of the expandable implant after releasing a primary constraining sleeve used for constraining the expandable implant toward a delivery configuration for endoluminal delivery; and methods of using the same.

18 Claims, 13 Drawing Sheets

Related U.S. Application Data continuation of application No. 14/608,922, filed on Jan. 29, 2015, now Pat. No. 10,524,944.

(60) Provisional application No. 61/933,227, filed on Jan. 29, 2014.

(51) Int. Cl.
    *A61F 2/966* (2013.01)
    *A61F 2/06* (2013.01)

(52) U.S. Cl.
    CPC ... *A61F 2002/065* (2013.01); *A61F 2250/001* (2013.01)

(58) Field of Classification Search
    CPC ........ A61F 2/9661; A61F 2/9662; A61F 2/97; A61F 2002/061; A61F 2002/067; A61F 2002/9665
    See application file for complete search history.

(56) References Cited

U.S. PATENT DOCUMENTS

| | | | |
|---|---|---|---|
| 6,352,561 B1 | 3/2002 | Leopold et al. | |
| 6,361,637 B2 | 3/2002 | Martin et al. | |
| 6,379,319 B1 | 4/2002 | Garibotto et al. | |
| 6,520,986 B2 | 2/2003 | Martin et al. | |
| 6,645,242 B1 | 11/2003 | Quinn | |
| 7,144,421 B2 | 12/2006 | Carpenter et al. | |
| 8,236,040 B2 | 8/2012 | Mayberry et al. | |
| 8,273,115 B2 | 9/2012 | Hamer et al. | |
| 8,663,306 B2 | 3/2014 | Kasprzak et al. | |
| 11,559,417 B1 | 1/2023 | Burkart et al. | |
| 2002/0143383 A1* | 10/2002 | Parodi | A61F 2/954 623/1.11 |
| 2004/0117003 A1 | 6/2004 | Ouriel et al. | |
| 2005/0182476 A1 | 8/2005 | Hartley et al. | |
| 2007/0083215 A1* | 4/2007 | Hamer | A61M 25/0662 606/108 |
| 2007/0179590 A1 | 8/2007 | Lu et al. | |
| 2008/0269866 A1 | 10/2008 | Hamer et al. | |
| 2008/0269867 A1* | 10/2008 | Johnson | A61F 2/954 623/1.11 |
| 2009/0259285 A1* | 10/2009 | Duane | A61F 2/958 604/164.13 |
| 2009/0259298 A1 | 10/2009 | Mayberry et al. | |
| 2011/0087318 A1 | 4/2011 | Daugherty et al. | |
| 2012/0109279 A1 | 5/2012 | Mayberry et al. | |
| 2012/0232645 A1 | 9/2012 | Machold et al. | |
| 2013/0030514 A1* | 1/2013 | Kasprzak | A61F 2/07 623/1.12 |
| 2013/0046371 A1 | 2/2013 | Greenberg et al. | |
| 2013/0123907 A1* | 5/2013 | Roeder | A61F 2/958 623/1.23 |
| 2013/0289713 A1* | 10/2013 | Pearson | A61F 2/954 623/1.35 |
| 2014/0257453 A1 | 9/2014 | Roeder | |
| 2014/0277355 A1 | 9/2014 | Roeder | |

FOREIGN PATENT DOCUMENTS

| | | | |
|---|---|---|---|
| WO | 2006/052322 A2 | 5/2006 | |
| WO | 2011/116308 A1 | 9/2011 | |

* cited by examiner

FIG. 3A
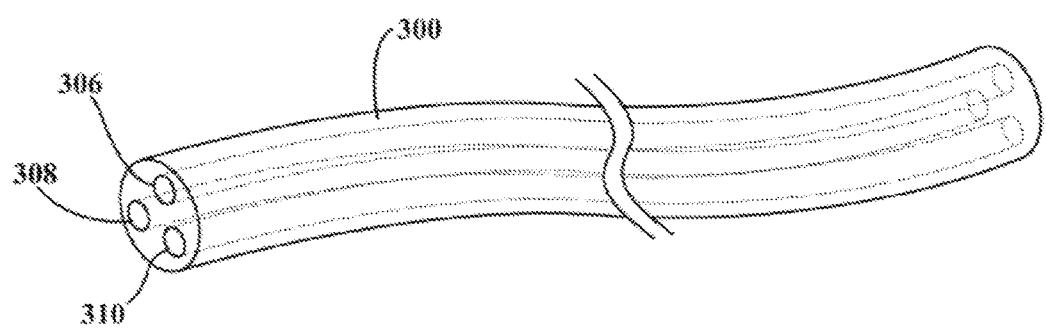
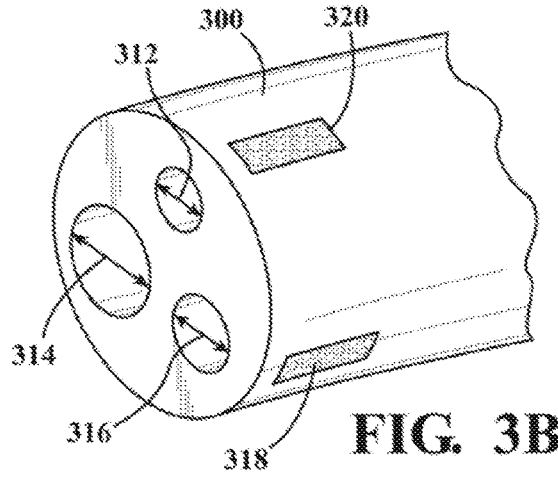
FIG. 3B
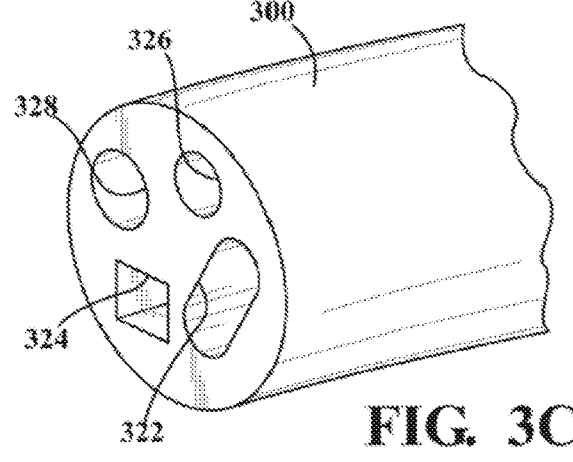
FIG. 3C
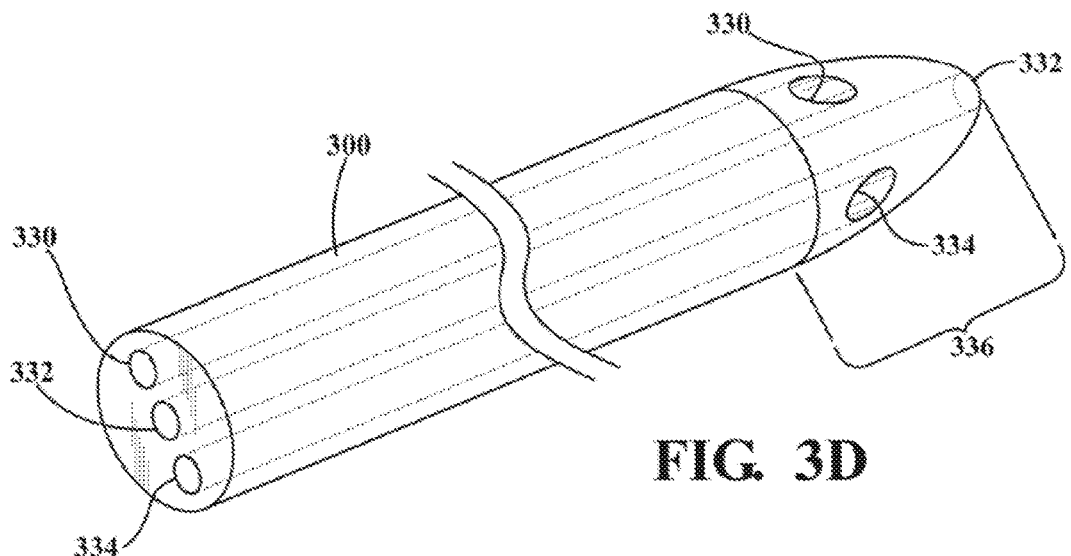
FIG. 3D

1

DELIVERY SYSTEMS AND METHODS OF ENDOLUMINAL DELIVERY OF BRANCHED VASCULAR ENDOPROSTHETIC DEVICES

CROSS-REFERENCE TO RELATED APPLICATION

This application is a continuation of U.S. patent application Ser. No. 16/690,388, filed Nov. 21, 2019, now U.S. Pat. No. 11,559,417, issued on Jan. 24, 2023, which is a continuation of U.S. patent application Ser. No. 14/608,922, filed Jan. 29, 2015, now U.S. Pat. No. 10,524,944, issued Jan. 7, 2020, which claims the benefit of U.S. Provisional Application 61/933,227, filed Jan. 29, 2014, all of which are incorporated herein by reference in their entireties for all purposes.

FIELD

The present disclosure relates to delivery systems and methods of endoluminally delivering branched vascular endoprosthetic devices to vascular treatment sites.

BACKGROUND

There is a need for advanced devices, tools, systems and methods used for the endoluminal treatment of aortic diseases, particularly in the descending aorta adjacent to the celiac artery, superior mesenteric artery and the two renal arteries. Such devices and methods can require four branch vessels along with the capability to engage an optional distal bifurcated device and an optional proximal extender device.

BRIEF DESCRIPTION OF THE DRAWINGS

The features and advantages of the present disclosure will become more apparent from the detailed description set forth below when taken in conjunction with the drawings.

FIG. 3A through 3D are perspective views of a three lumen catheter having optional shaped lumens and a proximal tapered end.

2

Figures 6A, 6B:
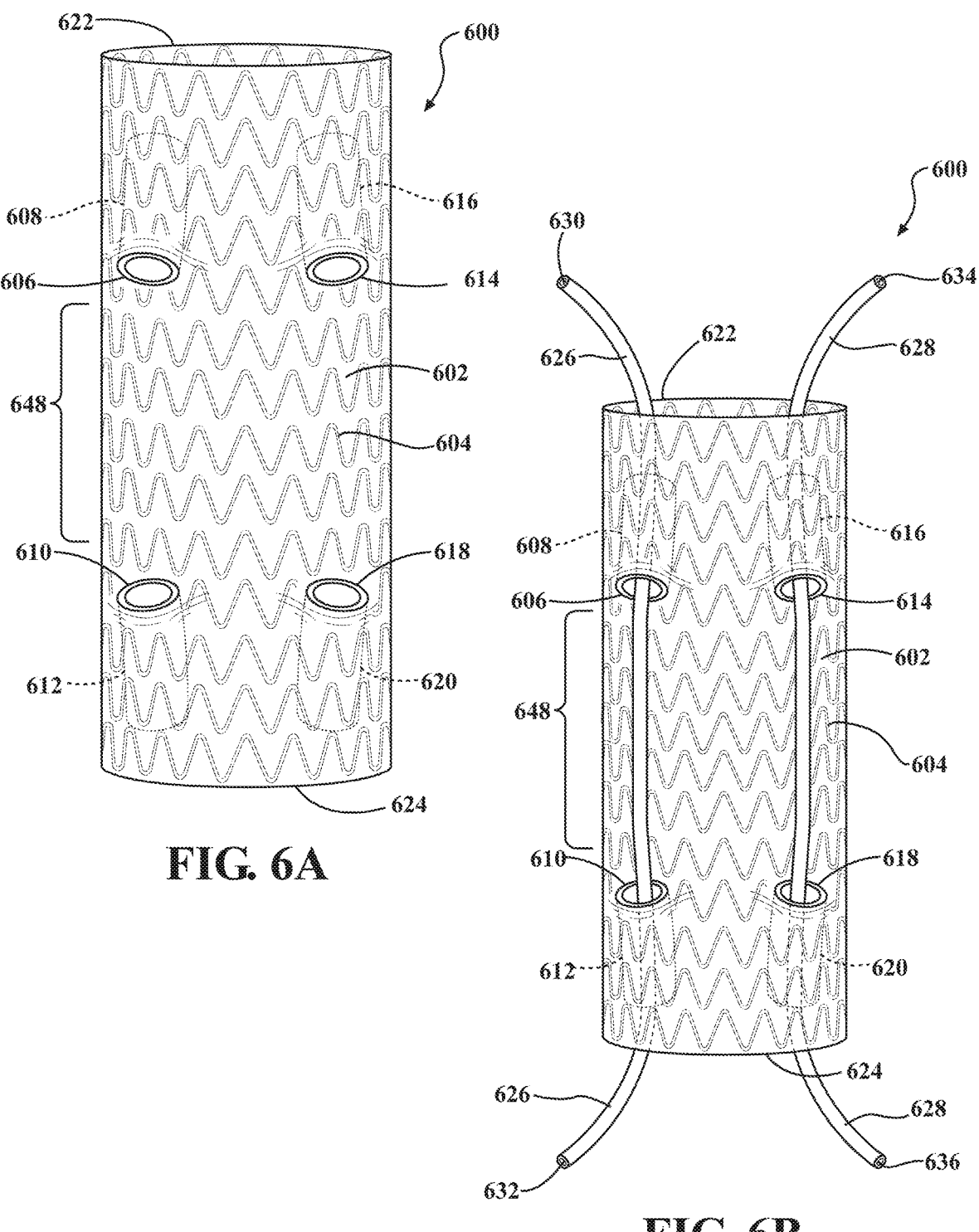
FIG. 6A is a perspective view of a stent graft having four side branch portals.
FIG. 6B is a perspective view of a stent graft having four side branch portals with two removable guidewire tubes placed through the four side branch portals.
Figures 6C, 6D:
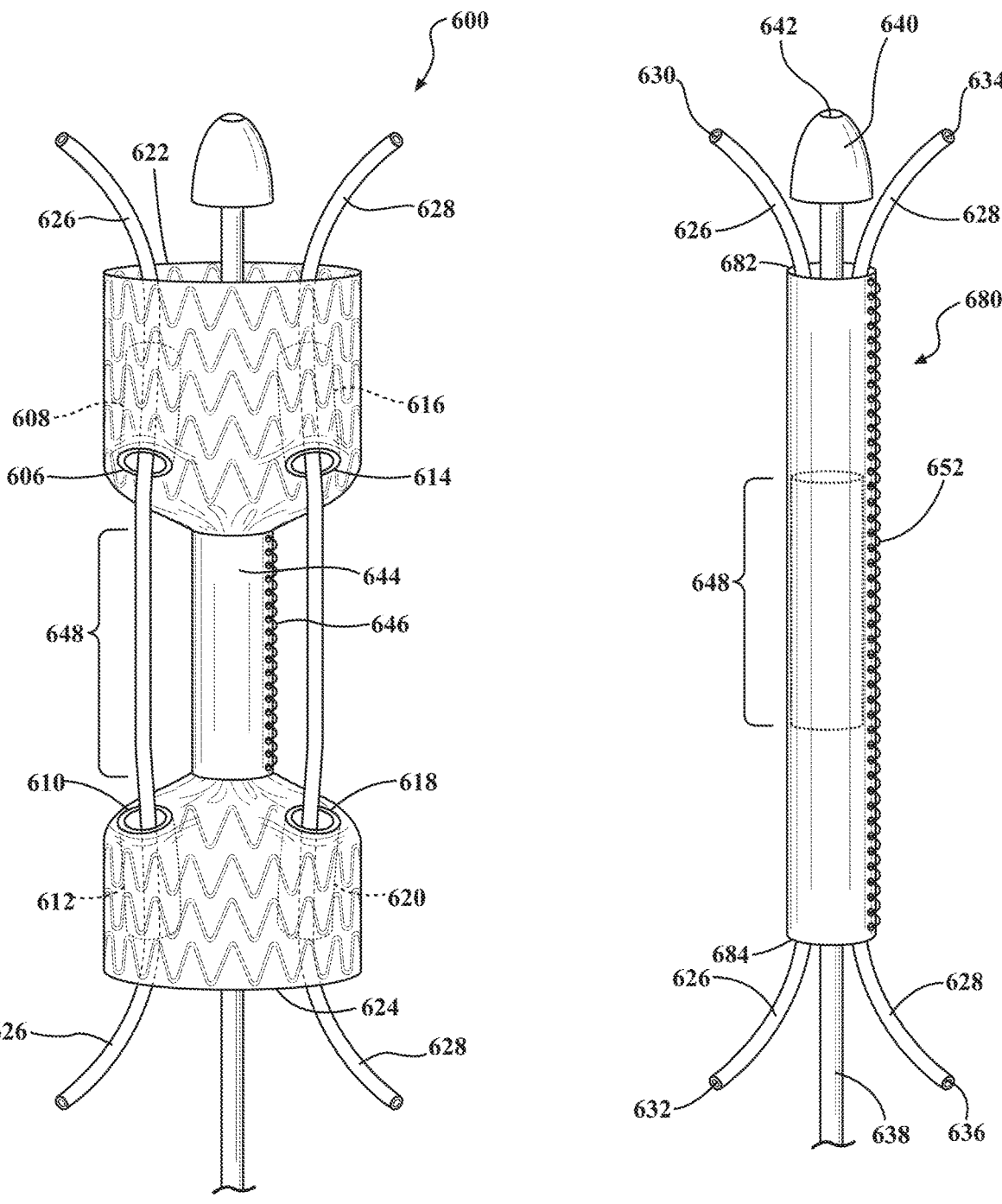
FIG. 6C is a perspective view of a stent graft having four side branch portals, two removable guidewire tubes. The mid-section of the stent graft is shown compressed onto a delivery catheter.

FIG. 6D is a perspective view of a stent graft having four side branch portals, two removable guidewire tubes. The stent graft is fully constrained in a compacted delivery state.

Figure 7:
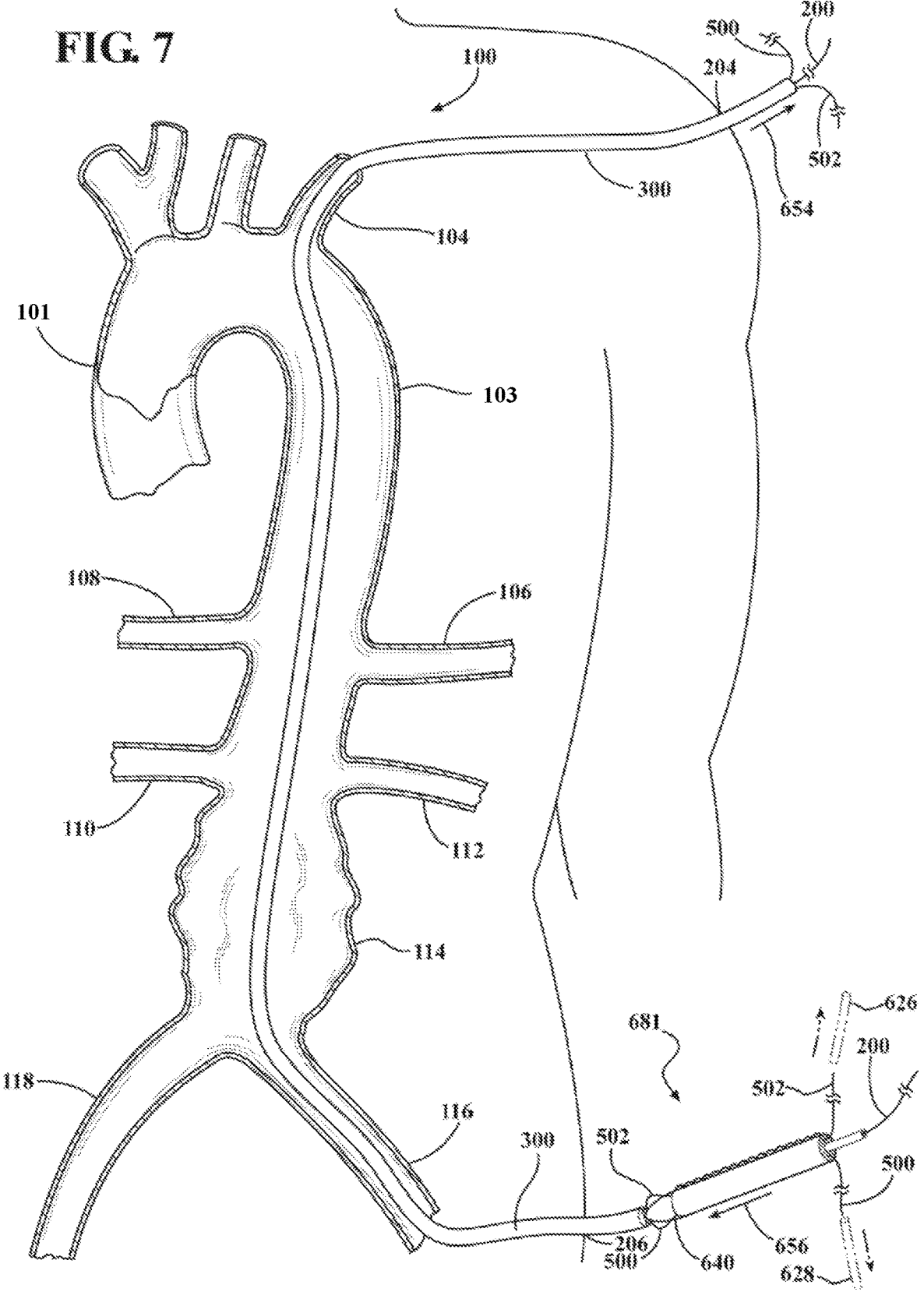

FIG. 7 is the cross-sectional representation of a human anatomy with a three lumen catheter with three guidewires extending out of upper and lower access sites and transversing the left subclavian artery, the aorta and a single iliac artery. A compacted stent graft is shown with the three guidewires routed through the compacted stent graft.

Figure 8:
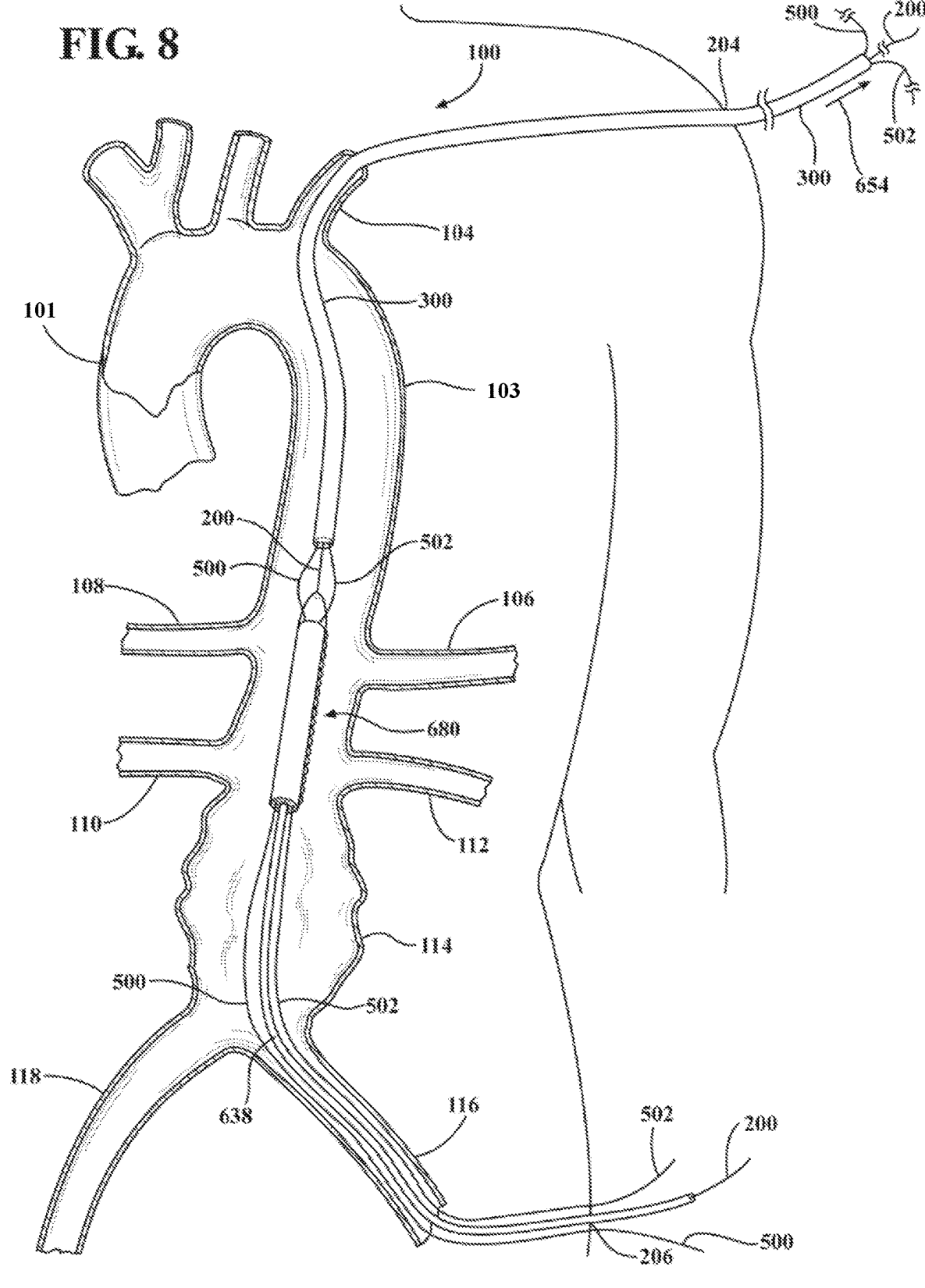

FIG. 8 is the cross-sectional representation of a human anatomy with a three lumen catheter with three guidewires extending out of upper and lower access sites and transversing the left subclavian artery, the aorta and a single iliac artery. A compacted stent graft is shown at the desired target site with the three guidewires routed through the compacted stent graft.

Figure 9:
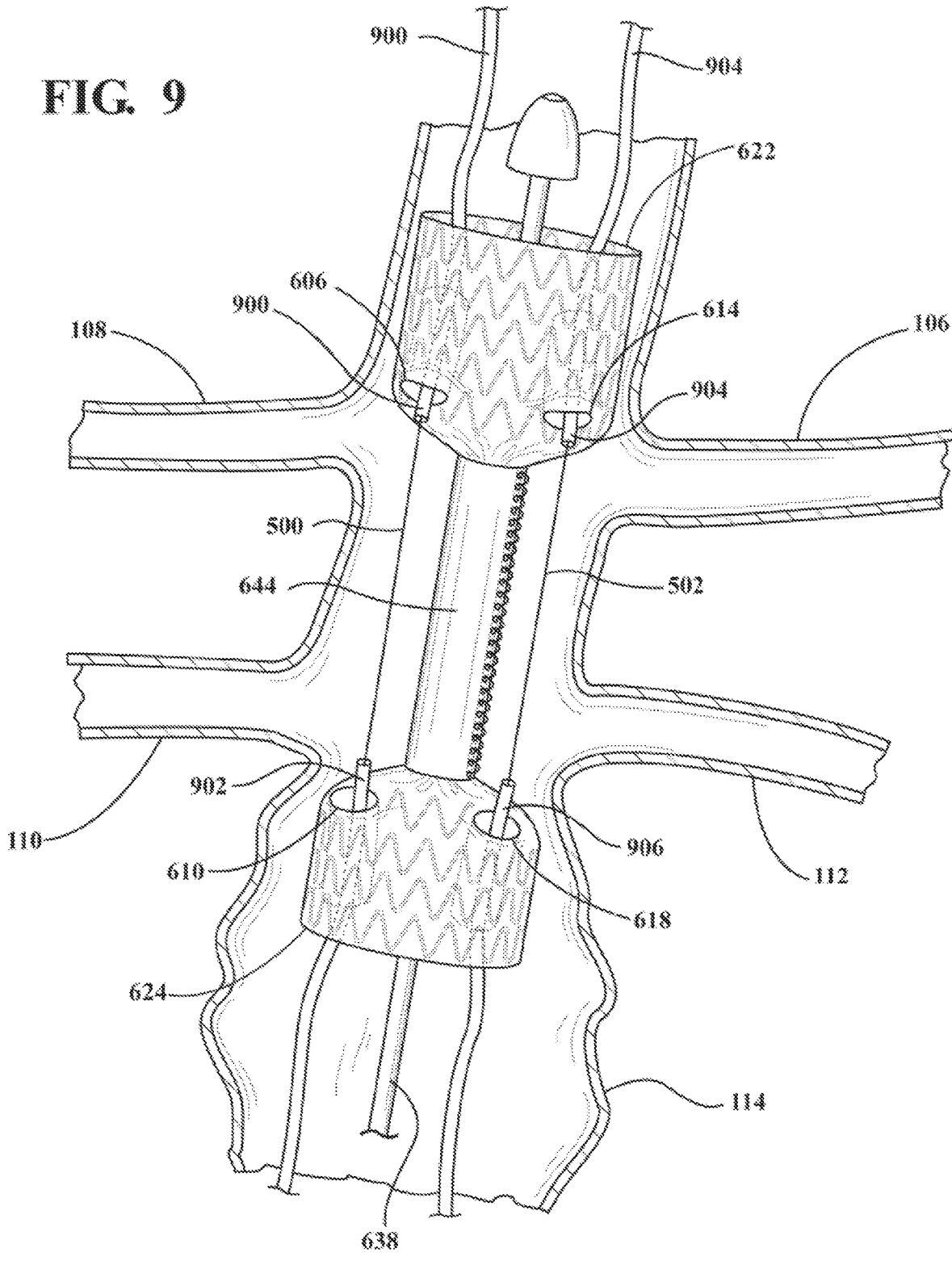

FIG. 9 is the cross-sectional representation of a human anatomy with a stent graft having a compacted mid-section along with expanded proximal and distal ends. Four guide catheters are shown routed over two guidewires.

Figure 10:
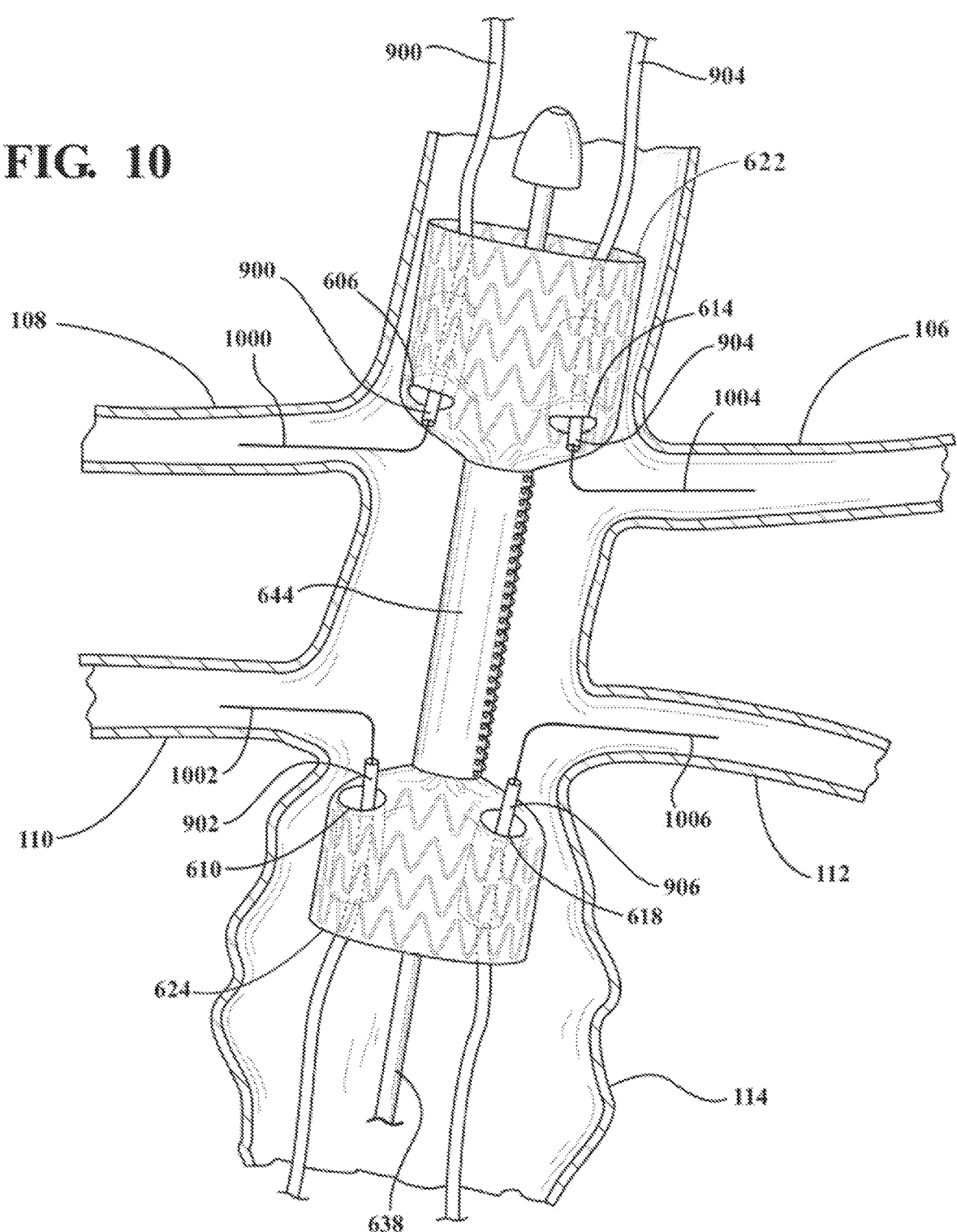

FIG. 10 is the cross-sectional representation of a human anatomy with a stent graft having a compacted mid-section along with expanded proximal and distal ends. Four side branch guidewires are shown routed through the four guide catheters and into four branch vessels.

Figure 11:
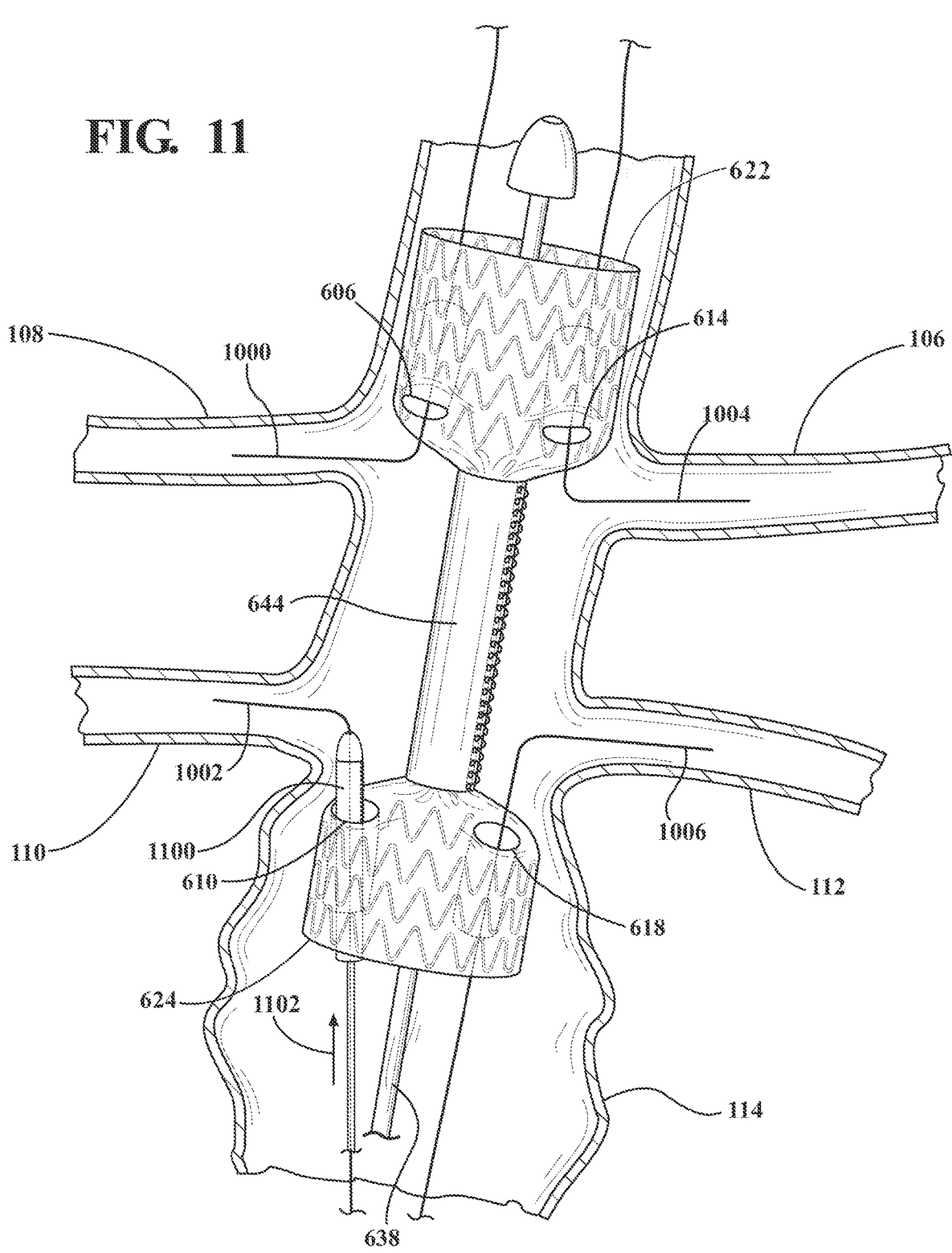

FIG. 11 is the cross-sectional representation of a human anatomy with a stent graft having a compacted mid-section along with expanded proximal and distal ends. Shown is a compacted side branch device being positioned into a branch vessel.

Figure 12:
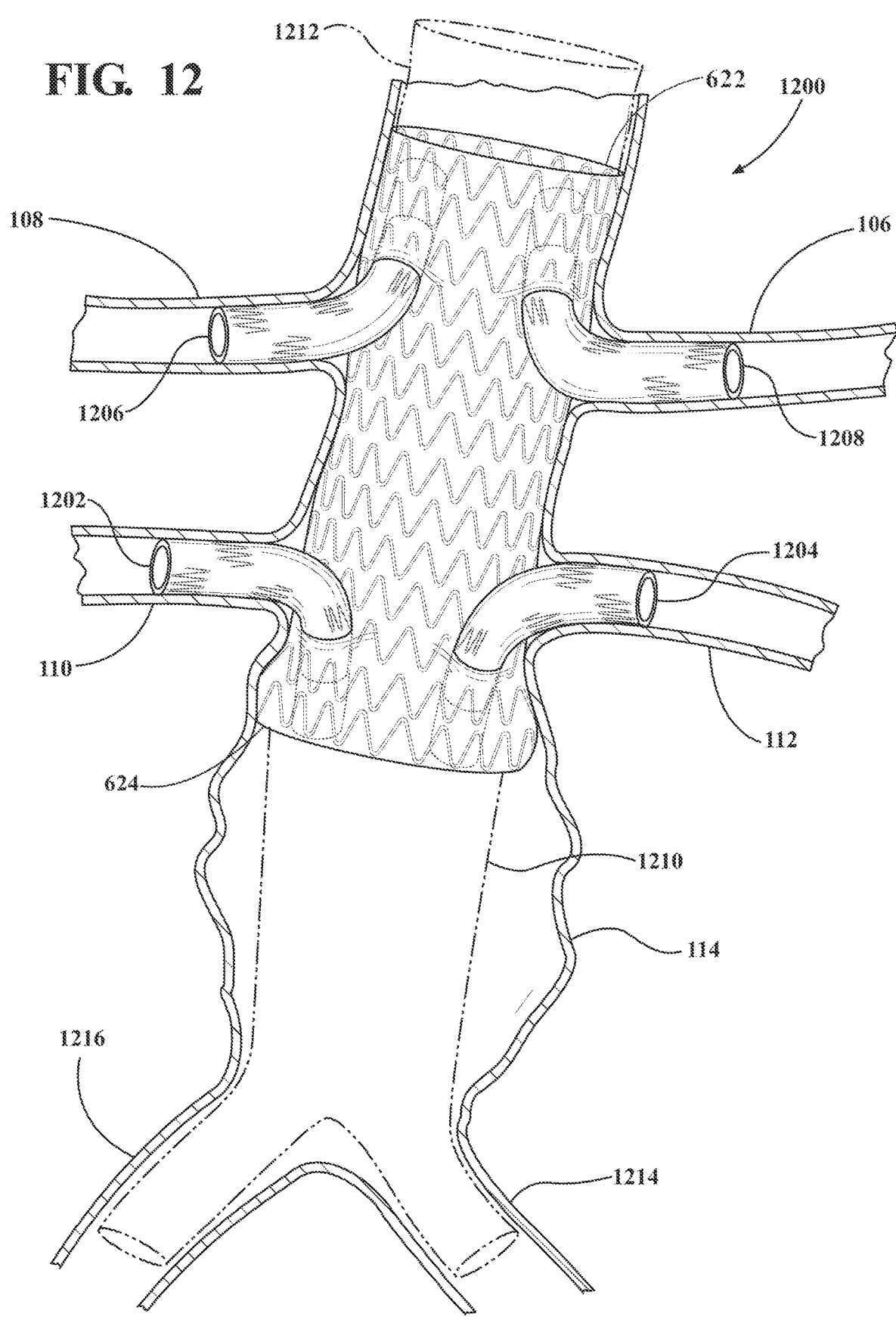

FIG. 12 is the cross-sectional representation of a human anatomy with a fully expanded stent graft having four branch devices expanded into four branch vessels.

DETAILED DESCRIPTION

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" refers to a location that is, or a portion of an endoluminal device (such as a stent-graft) that when implanted is, further downstream with respect to blood flow than another portion of the device. Similarly, the term "distally" refers to the direction of blood flow or further downstream in the direction of blood flow.

The term "proximal" refers to a location that is, or a portion of an endoluminal device that when implanted is, further upstream with respect to blood flow than another portion of the device. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

Throughout this specification and in the claims, the term "leading" refers to a relative location on a device which is closer to the end of the device that is inserted into and progressed through the vasculature of a patient. The term "trailing" refers to a relative location on a device which is closer to the end of the device that is located outside of the vasculature of a patient.

Devices, systems and methods of endoluminally delivering a branchable expandable implant in accordance with various embodiments are disclosed herein for treating disease of human vasculature. Although the description below and figures are illustrated in the context of treating the aorta 100, including the ascending aorta 101, aortic arch 102, and descending aorta 103, it should be appreciated that the present disclosure can be applied to treatment of other portions of the vasculature, including, for example, any disease where a larger vessel and one or more branch vessels are to be treated.

Figure 1:
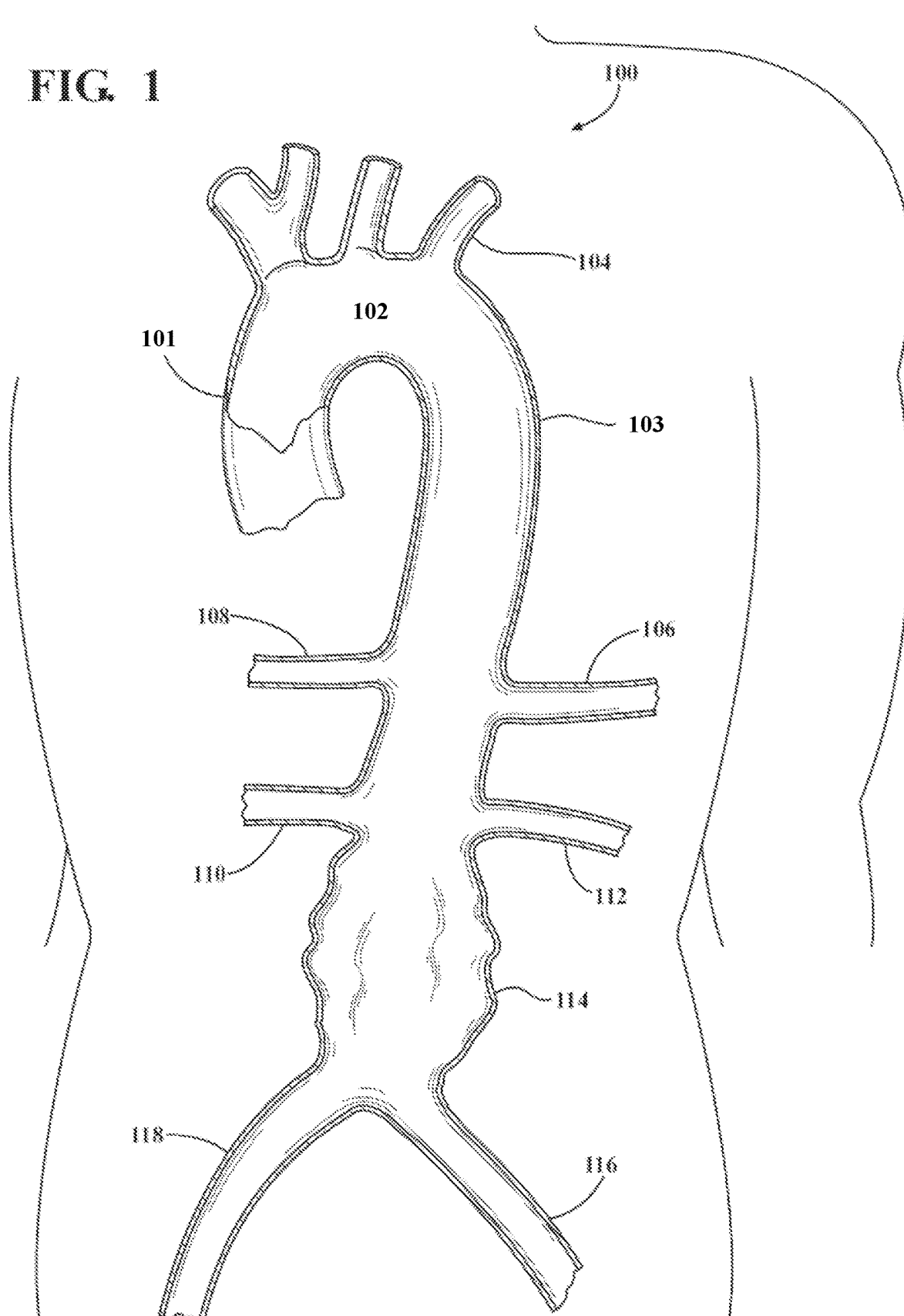
FIG. 1 is a cross-sectional representation of a human anatomy showing an aorta, left subclavian artery, celiac artery, superior mesenteric artery, two renal arteries and two iliac arteries.
Figure 2:
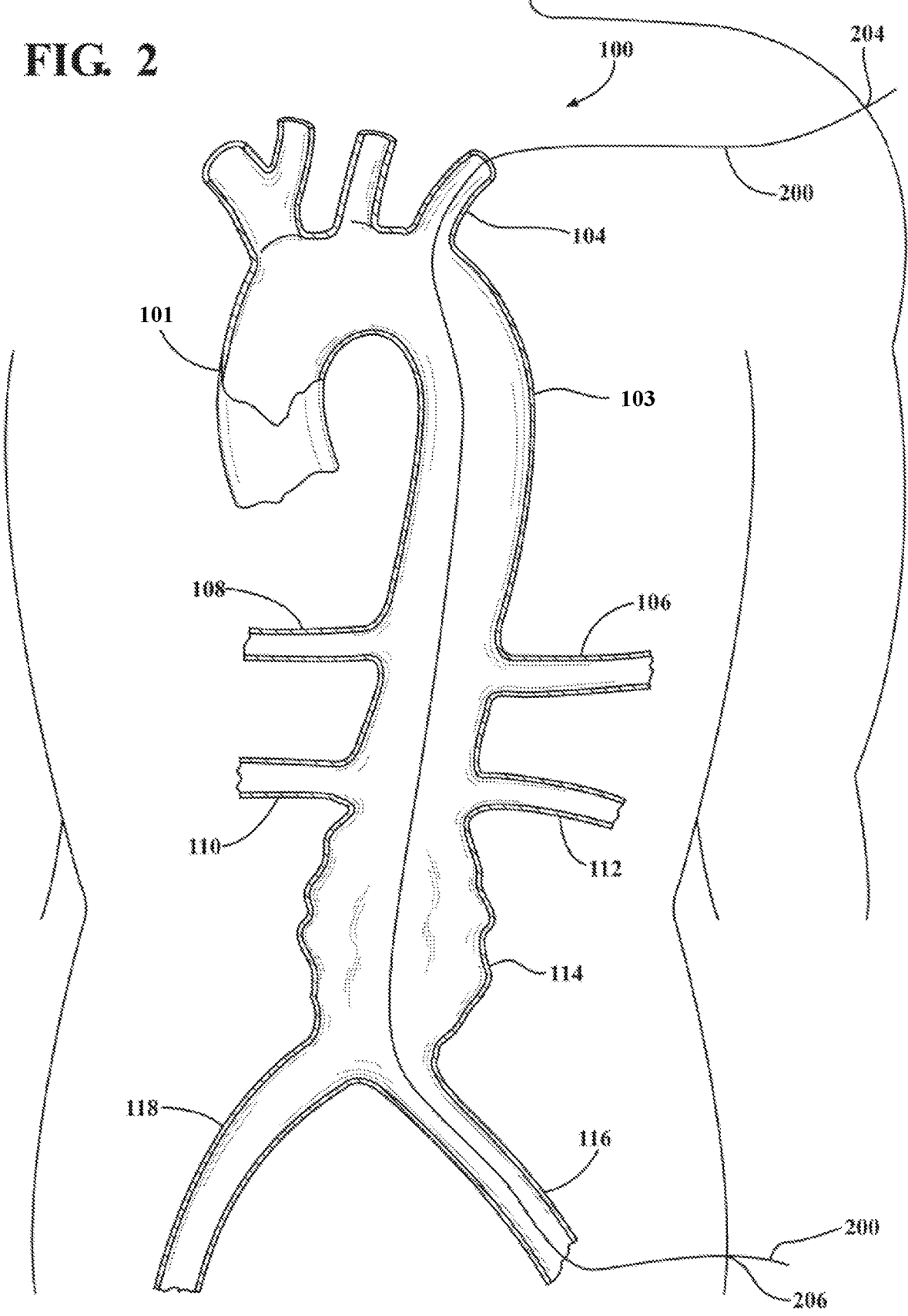
FIG. 2 is the cross-sectional representation of a human anatomy with a guidewire extending out of upper and lower access sites and transversing the left subclavian artery, the aorta and a single iliac artery.

In various embodiments, a method of endoluminally delivering a branchable expandable implant can include inserting a first guidewire into the vasculature through one of a first access site and second access site, through the vasculature to be treated, and out of the other of the first access site and second access site, such that the guidewire extends through the vasculature to be treated and opposite ends of the first guidewire extend outside of the body through respective access sites. As shown in FIG. 2, for example, a first guidewire 200 is inserted into the left subclavian artery (LSA) 104 through a first access site 204, routed through the descending aorta 103 and one of the iliac arteries 116 and 118, and out of the second access site 206, such that the first guidewire 200 extends through the aorta 100 and, more specifically, through the treatment site 114, and opposite ends of the first guidewire 200 extend outwardly from the body from respective access sites 204, 206.

Figure 4:
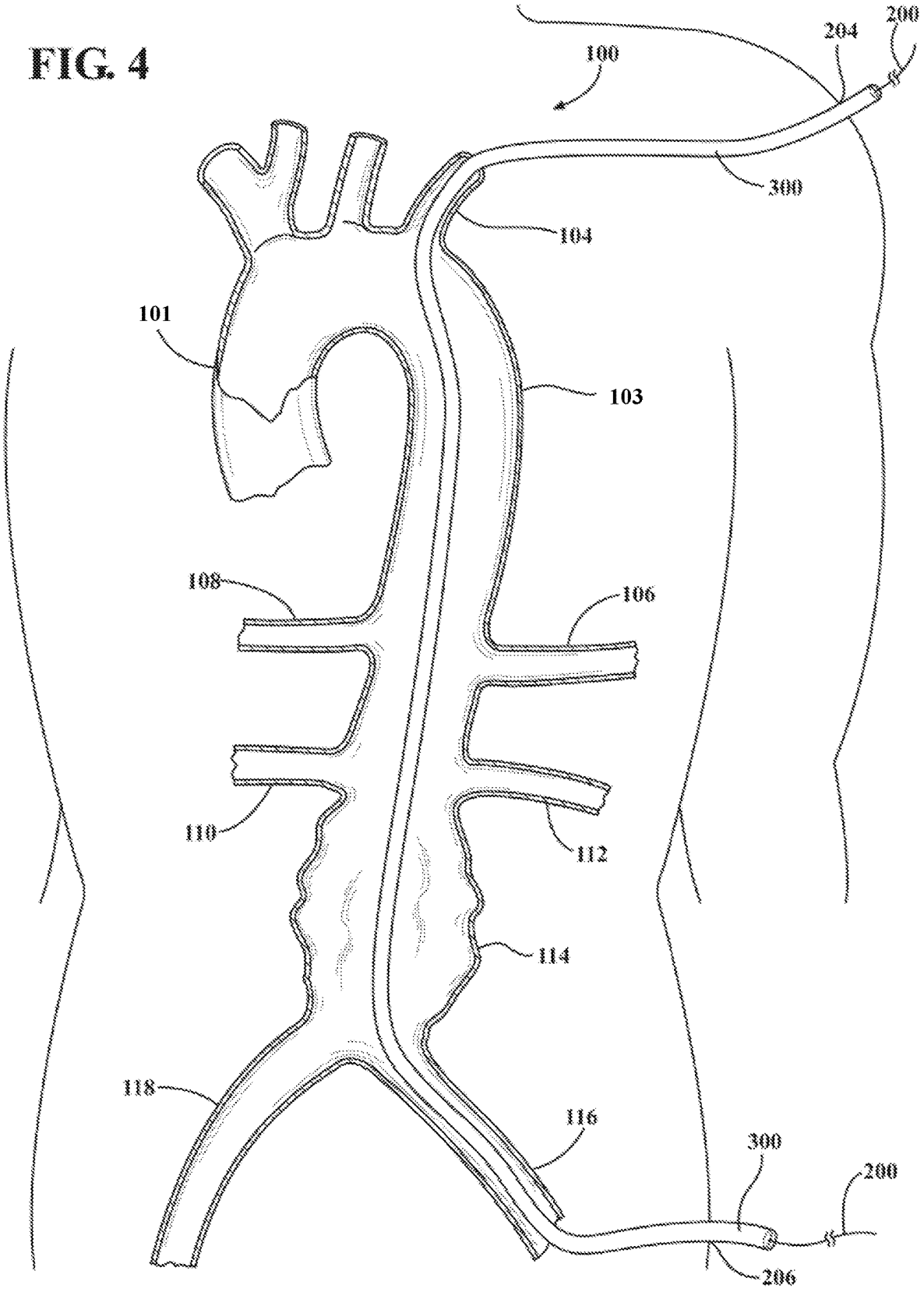
FIG. 4 is the cross-sectional representation of a human anatomy with a three lumen catheter and a guidewire extending out of upper and lower access sites and transversing the left subclavian artery, the aorta and a single iliac artery.

The method also includes inserting an end of the first guidewire into a leading end of an elongated delivery member, such as an introducer sheath or catheter, and inserting the leading end of the elongated delivery member into the vasculature along the first guidewire through one of the first and second access sites, and pushing the elongated delivery member along the first guidewire through the vasculature until the leading end exits the body through the other of the one of the first and second access sites. For example, as illustrated in FIG. 4, the first guidewire 200 is inserted into a leading end of a first catheter 300 and the first catheter 300 is passed along the first guidewire 200 and into the vasculature via the first access site 204. The first catheter 200 is pushed until the leading end of the first catheter 200 exits the iliac and/or femoral artery and the body through the second access site 206. Thus, the first guidewire 200 and first catheter 300 extend through the aorta and, more specifically, through the treatment site 114, and opposite ends of each of the first guidewire 200 and first catheter 300 extend outwardly from the body from respective access sites 204, 206.

Catheters, introducer sheaths, hubs, handles and other components usable in medical device delivery systems and methods disclosed herein can be constructed using any suitable medical grade material or combination of materials using any suitable manufacturing process or tooling. Suitable medical grade materials can include, for example, nylon, polyacrylamide, polycarbonate, polyethylene, poly-formaldehyde, polymethylmethacrylate, polypropylene, polytetrafluoroethylene, expanded polytetrafluoroethylene, polytrifluorochlorethylene, polyvinylchloride, polyurethane, elastomeric organosilicon polymers, Pebax® polyether block amide, and metals such as stainless steels and nitinol. Catheters can also include a reinforcing member, such as a layer of metal braid.

Figure 5:
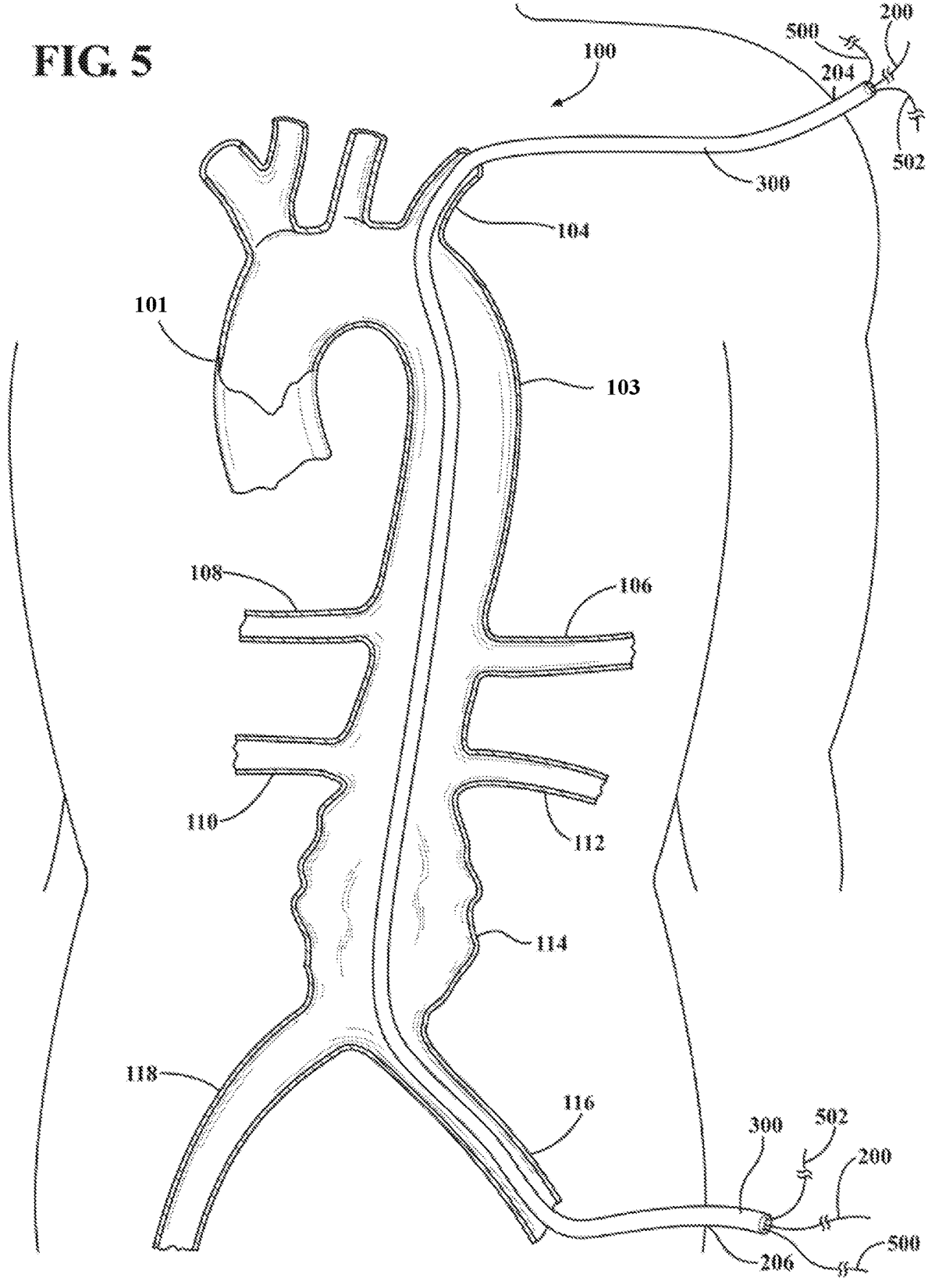
FIG. 5 is the cross-sectional representation of a human anatomy with a three lumen catheter with three guidewires extending out of upper and lower access sites and transversing the left subclavian artery, the aorta and a single iliac artery.

The method also includes inserting a second guidewire completely through the first catheter, such that opposite ends of the second guidewire extends outwardly from the body from respective access sites. As necessary, a third guidewire can be inserted completely through the first catheter, such that opposite ends of the third guidewire extends outwardly from the body from respective access sites. As shown in FIG. 5, for example, a second guidewire 500 and a third guidewire 502 are each routed completely through the first catheter 300 and, therefore, through the vasculature 100 and treatment site 114, such that opposite ends of each of the second 500 and third 502 guidewires extend outwardly from respective access sites 204, 206 via respective opposite ends of the first catheter 300.

In various embodiments, a catheter having a plurality of lumens for managing a plurality of guidewires can be provided and used in methods disclosed herein. As shown in FIGS. 3A-3D, for example, the first catheter 300 can include first 306, second 308 and third 310 lumens for receiving the first 200, second 500 and third 502 guidewires, respectively, therethrough. The lumens can be provided in varying diameters, as illustrated at 312, 314, 316 in FIG. 3B. The lumens can also be provided in varying cross-sectional shapes, as illustrated at 322, 324, 326, 328 in FIG. 3C. Further, the lumens can be provided in cross section in a variety of orientations relative to each other. For example, as shown in FIG. 3D, the lumens 330, 332, 334 are shown arranged linearly in cross section. Still referring to FIG. 3D, the first catheter 300 can include a distal olive 336, wherein the lumens 330, 332, 334 in the first catheter 300 extend through the distal olive 336 to allow the guidewires to pass through both the catheter and the distal olive.

Referring back to FIG. 3B, the first catheter 300 can also include radiopaque markers 318, 320 to facilitate viewing on an x-ray fluoroscope during an implantation procedure. Any number, shape and location of radiopaque markers can be utilized as needed.

Delivery systems and methods disclosed herein are particularly suited for endoluminal delivery of branchable expandable implants for treating branched vasculature. Expandable implants can include, for example, stents, grafts, and stent grafts. Further, expandable implants can include one or more stent components 604 with one or more graft members disposed over and/or under the stent, which can dilate from a delivery configuration, through a range of larger intermediary configurations, and toward a deployed configuration engaged with vessel walls at a treatment site. However, and as discussed below, any suitable combination and configuration of stent component(s) and graft member(s) is within the scope of the present disclosure. For example, stent components can have various configurations such as, for example, rings, cut tubes, wound wires (or ribbons) or flat patterned sheets rolled into a tubular form. Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly (caprolactones), poly(lactic/glycolic acid) polymers, poly (hydroxybutyrates) and poly(orthoesters).

Moreover, potential materials for graft members include, for example, expanded polytetrafluoroethylene (ePTFE), polyester, polyurethane, fluoropolymers, such as perfluoroelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member may include a bioactive agent. In one embodiment, an ePTFE graft includes a carbon component along a blood contacting surface thereof. Any graft member which can be delivered by a catheter is in accordance with the present disclosure. Further detail of materials and general construction of stents, graft members and stent grafts are generally disclosed in U.S. Pat. Nos. 6,042,605; 6,361,637; and 6,520,986 all to Martin et al.

In various embodiments, a stent component and/or graft member can comprise a therapeutic coating. In these embodiments, the interior and/or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

Referring to FIG. 6A, for example, a branchable expandable implant 600 can be provided having opposite proximal 622 and distal 624 ends, a main lumen extending axially between the proximal 622 and distal 624 ends, and branch portals 606, 610, 614, 618 for receiving respective branch devices therethrough for directing a portion of blood flow from the main lumen to branch vessels. In various embodiments, the branch portals can be arranged in pairs 606, 614 and 610, 618 on opposite sides of a middle section 602 of the expandable implant 600. Other locations, arrangements or groupings of branch portals can be utilized depending on the vessel and branch vessels to be treated. Further, branch portals can face in the proximal direction, distal direction, radially outwardly facing, any angles relative to the main lumen axis, or any combination thereof.

Still referring to FIG. 6A, the expandable implant 600 can also include internal branch supports 608, 612, 616, 620, which are in fluid communication with respective branch portals 606, 610, 614, 618 and which provide support to and maintain orientation of branch devices extending therethrough. Further detail of materials and general construction of internal branch supports are generally disclosed in U.S. Pat. No. 6,645,242 to Quinn and in US 2011/0087318 to Daugherty et al.

Delivery systems and methods in accordance with various embodiments disclosed herein can utilize removable guidewires to preserve branch portals for guidewire cannulation therethrough subsequent to compacting the expandable implant toward a delivery configuration for endoluminal delivery to the treatment site. As shown in FIG. 6B, for example, a first removable guidewire tube 626 can be inserted through branch portals 606, 610 from each branch portal pair. Similarly, a second removable guidewire tube 628 can be inserted through the other branch portals 614, 618 from each branch portal pair. Opposite ends 630, 632 and 634, 636 of the first 626 and second 628 removable guidewire tubes extend axially beyond the proximal 622 and distal 624 ends of the expandable implant 600, respectively. Removable guidewire tube can comprise the same materials listed above for the catheter materials. Further details of materials and general construction of removable guidewire tubes are described in U.S. Pat. No. 8,273,115 to Hamer et al.

In various embodiments, a branchable vascular endoprosthetic device with one or more removable guidewire tubes extending through branch portals thereof can be radially compacted and retained on a delivery catheter in a delivery configuration for endoluminal delivery to the treatment site. For example, as shown in FIG. 6D, the expandable implant 600 is coupled to and supported on a delivery catheter 638 adjacent a distal end of the delivery catheter 638. A distal olive 640 is fixedly secured to distal end of the delivery catheter 638. A lumen 642 extends axially through the length of the delivery catheter 638 and the distal olive 640 to allow a guidewire to be fed therethrough. A primary constraining sleeve 680 extends over and releasably constrains the expandable implant 600 toward a compacted delivery configuration. An elongated first coupling member 652, such as a fiber or wire, stitches opposing edges or sides of the primary constraining sleeve together to releasably constrain the expandable implant 600. The primary constraining sleeve 680 can be opened by de-coupling the first coupling member 652 from the primary constraining sleeve 680. Further details of materials and general construction of constraining sleeves can be found in U.S. Pat. No. 6,352,561 to Leopold et al.

Opposite proximal 630, 634 and distal 632, 636 ends of each removable guidewire tube 626, 628 extend beyond respective opposite ends 682 and 684 of the primary constraining sleeve 680 to allow guidewires to be routed through the branch portals 606, 610, 614, 618 via the removable guidewire tubes 626, 628 even though the expandable implant is radially inwardly compressed toward or otherwise covered while in the delivery configuration by the primary constraining sleeve 680.

In various embodiments, one or more intermediate constraining sleeves can be utilized to releasably retain any portion or portions of a branchable vascular endoprosthetic device toward the delivery configuration or, alternatively, an intermediate configuration after opening or release of the primary constraining sleeve, wherein the intermediate configuration is larger than the delivery configuration and yet still smaller than a deployed configuration engaged with the vasculature. As illustrated in FIG. 6C, for example, a secondary constraining sleeve 644 extends over the middle portion 648 and releasably retains the middle portion 648 toward the delivery configuration after opening the primary sleeve. Alternatively, the secondary constraining sleeve can be sized to retain the middle portion toward an intermediate configuration which is larger than the delivery configuration and smaller than the deployed configuration. An elongated second coupling member 646 stitches opposing edges or sides of the secondary constraining sleeve 644 together to releasably constrain the middle portion 648 of the expandable implant 600.

By this arrangement, the expandable implant can be deployed in a staged sequence, wherein the primary constraining sleeve is opened first to allow the portions of the expandable implant that are not retained by the secondary sleeve to expand outwardly toward a deployed configuration engaged with the vessel walls. As illustrated in FIG. 6C, for example, proximal 622 and distal 624 ends of the expandable implant 600, which are not constrained by the secondary constraining sleeve 644 are allowed to expand toward the deployed configuration after opening the primary constraining sleeve.

Alternatively, a single coupling member may be utilized to stitch both the primary and secondary constraining sleeves. By this arrangement, the single coupling member can be decoupled from the primary and secondary constraining sleeves in sequence to render a staged deployment.

Alternatively, one or more secondary or intermediate constraining sleeves can be utilized releasably constrain one or more portions of the expandable implant after opening the primary constraining sleeve.

Referring to FIG. 7, the first guidewire 200 is inserted and routed through the distal olive 640 and delivery catheter 638 via the lumen 642. The second 500 and third 502 guidewires are routed through completely the first 626 and second 628 removable guidewire tubes and, therefore, beneath the primary constraining sleeve 600 and through the branch portals 606, 610 and 614, 618, respectively. With the second 500 and third 502 guidewires in place, the first 626 and second 628 removable guidewire tubes can be removed from the expandable implant 600, as indicated by the arrows in FIG. 7. Thus, a delivery catheter assembly 681 comprising the expandable implant 600 coupled to the delivery catheter 638 and releasably retained by the primary 680 and secondary 644 constraining sleeves is loaded onto the first 200, second 500 and third 502 guidewires for endoluminal delivery to the treatment site 114. The delivery catheter assembly 681 is pushed toward abutment or engagement with the first catheter 300. Abutment or engagement between the delivery catheter assembly 681 and the first catheter 300 can occur outside the access vessel, for example as shown in FIG. 7, or alternatively within an access sheath previously placed within the access vessel.

Referring to FIG. 8, the first catheter 300 and delivery catheter 638 are displaced together along and guided by the guidewires 200, 500, 502 proximally or in a direction indicated by arrow 654. The delivery catheter assembly 681 enters the vasculature 102 through the second access site 206 and displaced toward the treatment site 114. The first catheter 300 and delivery catheter 638 remain abutted as they are displaced along the guidewires 200, 500, 502. At the treatment site, the first catheter 300 and delivery catheter 638 can be pushed, pulled and rotated to position the expandable implant 600 to a desired location and orientation at the treatment site 114. Abutment of the first catheter 300 and delivery catheter 638 facilitates fine adjustments until the desired location and orientation at the treatment site is achieved. Conventional fluoroscopy techniques utilizing radiopaque markers on any one or multiple components of the delivery catheter assembly can be utilized to facilitate positioning of the expandable implant at the treatment site. For example, radiopaque markers can be located at or near the branch portals to facilitate orientation of the branch portals relative to the branch vessels 106, 108, 110, 112 to be treated.

After the desired position and orientation of the expandable implant is achieved, the primary constraining sleeve can be opened to allow portions of the expandable implant not constrained by secondary constraining sleeve to expand outwardly toward the deployed configuration either engaged with the vessel walls at the treatment site or at least fully expanded. As shown in FIG. 9, for example, opening the primary constraining sleeve 680 allows the proximal 622 and distal 624 ends of the expandable implant 600 to expand outwardly toward the deployed configuration. For the condition specifically shown in FIG. 9, where an aneurysmal sac is located below the branch vessels to be treated, the proximal end 622 engages the vessel wall above the branch vessels to be treated or, more particularly engages healthy vessel wall tissue above the celiac 106 and mesentery 108 arteries. The distal end 624 extends into the aneurysmal space at the treatment site 114.

The middle portion 648 between the proximal 622 and distal 624 ends of the expandable implant 600 remains constrained by the secondary constraining sleeve 644, thereby leaving a space between the vessel walls and the middle portion 648 to facilitate maneuvering of guidewire, catheters, devices and potentially other tools used to deliver, position and deploy branch devices in the branch portals and branch vessels.

Still referring to FIG. 9, guide or branch catheters 900, 902, 904, 906 are inserted into respective branch supports 608, 612, 616, 620 and through branch portals 606, 610, 614, 618 of the expandable implant 600 along the first 500 and second 502 guidewires, such that leading tips of each of the branch catheter assemblies 900, 902, 904, 906 extend into the space between the vessel walls and the middle portion 648. The first 500 and second 502 guidewires can then be removed from the body.

Referring to FIG. 10, branch guidewires 1000, 1002, 1004, 1006 are inserted through lumens of respective branch catheters 900, 902, 904, 906 and introduced into the space between the vessel walls and the middle portion 648 of the expandable implant 600. The branch guidewires 1000, 1002, 1004, 1006 are then manipulated into branch vessels 106, 108, 110, 112.

Referring to FIG. 11, the branch catheters 900, 902, 904, 906 are removed from the body, thereby leaving the branch guidewires 1000, 1002, 1004, 1006 in place extending through branch portals 606, 610, 614, 618 and into branch vessels 106, 108, 110, 112 to provide means for guiding 1102 branch catheter assemblies carrying branch devices 1100 into the branch vessels 106, 108, 110, 112.

Referring to FIG. 12, branch catheter assemblies (not shown) carrying branch devices constrained toward delivery configurations for endoluminal delivery, in a manner as described above with respect to the expandable implant, are delivered along branch guidewires 1000, 1002, 1004, 1006 and introduced into respective branch vessels 106, 108, 110, 112. The branch devices 1206, 1202, 1208, 1204, as illustrated in FIG. 12, are allowed to expand and engage the branch supports 608, 612, 616, 620 and branch vessels 108, 110, 106, 112, respectively.

For the specific condition illustrated in FIG. 12, a conventional aneurysmal excluder device can be deployed in the aneurysmal space at the treatment site 114 and coupled to the distal end 624 of the expandable implant 600, thereby completing exclusion of the aneurysmal space from normal blood flow. In situations where the aneurysm is located in other portions of the vasculature, for example, along the aorta between or among the branch vessels to be treated, for example between the superior mesenteric/celiac arteries 106, 108 and the renal arteries 110, 112, the proximal 622 and distal 624 ends of the expandable implant 600 can be deployed to engage healthy vessel tissue on opposite sides of the branch vessel grouping 106, 108, 110, 112. In either case or various other conditions, conventional extender stent graft devices can be deployed to extend from the proximal 622 and/or distal ends 624 of the expandable implant.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A delivery system comprising:
a delivery catheter having a leading end and a trailing end;
a medical implant carried by the delivery catheter between the leading end and the trailing end of the delivery catheter, the medical implant having a proximal end and a distal end, with a main lumen extending between the proximal and distal ends, a middle portion between the proximal and distal ends, and a plurality of proximal branch portals and a plurality of distal branch portals located distal to the plurality of proximal branch portals, each of the proximal and distal branch portals being disposed proximate to the middle portion of the medical implant;
a first constraint configured to releasably maintain at least a proximal portion of the medical implant in a delivery configuration;
a second constraint configured to releasably maintain at least the middle portion at a diameter that is less than a fully deployed diameter of the medical implant following release of the first constraint;
a plurality of removable tubes, at least one of the plurality of removable tubes positioned through at least one of the plurality of proximal branch portals or at least one of the plurality of distal branch portals for cannulation thereof and extending into the proximal end of the medical implant, through the main lumen of the medical implant, and through the proximal and distal branch portals of the medical implant;
a multi-lumen catheter having a distal end and a proximal end, the multi-lumen catheter defining a first lumen and a second lumen extending between the distal end and the proximal end;
a first guidewire configured to extend through the first lumen of the multi-lumen catheter and a delivery lumen of the delivery catheter; and
a second guidewire configured to extend through the second lumen of the multi-lumen catheter and along at least a portion of the removable tubes,
wherein the multi-lumen catheter and the delivery catheter are displaceable together along and guided by the first guidewire and the second guidewire to deliver the medical implant.

2. The delivery system of claim 1, wherein the first lumen has a first diameter and the second lumen has a second diameter different from the first diameter.

3. The delivery system of claim 1, wherein the first lumen has a first cross-sectional shape and the second lumen has a second cross-sectional shape different from the first cross-sectional shape.

4. The delivery system of claim 1, further comprising a third guidewire and the multi-lumen catheter has a third lumen configured to receive the third guidewire.

5. The delivery system of claim 4, wherein the multi-lumen catheter defines a length, and the first, second, and third lumens extend parallel to one another along the length of the multi-lumen catheter.

6. The delivery system of claim 1, wherein the multi-lumen catheter further includes a multi-lumen catheter olive disposed at the distal end thereof through which each of the first and second lumens extends.

7. The delivery system of claim 1, wherein the multi-lumen catheter further includes a plurality of radiopaque markers.

8. The delivery system of claim 1, wherein the delivery catheter further includes a delivery catheter olive disposed at the leading end thereof and through which the delivery lumen extends.

9. The delivery system of claim 1, wherein the leading end of the delivery catheter is operable to be engaged with the proximal end of the multi-lumen catheter when the multi-lumen catheter and the delivery catheter are positioned together along the first guidewire and the second guidewire.

10. The delivery system of claim 1, wherein the second guidewire extends externally along the delivery catheter such that a first portion of the second guidewire extends within the medical implant, and a second portion of the second guidewire extends externally along the medical implant.

11. A method of delivering a medical implant to a vasculature of a body, the method comprising:
routing a first guidewire through a first lumen of a multi-lumen catheter extending between a distal end and a proximal end of the multi-lumen catheter;
providing a delivery catheter having a leading end and a trailing end, the delivery catheter carrying a medical implant that includes a plurality of branch portals between the leading end and the trailing end of the delivery catheter, such that the leading end of the delivery catheter is disposed adjacent to the proximal end of the multi-lumen catheter, the medical implant being constrained by a first constraint and a second constraint;
positioning at least one of a plurality of removable tubes through at least one of the branch portals for cannulation of the branch portals;
extending a second guidewire through a second lumen and along at least a portion of the removable tubes, the second lumen extending between the distal end and the proximal end of the multi-lumen catheter;
inserting the multi-lumen catheter into the vasculature through a first access site of the body;
inserting the first guidewire through a delivery lumen of the delivery catheter;
inserting the delivery catheter into the vasculature through a second access site of the body that is different from the first access site;
abutting the delivery catheter against the multi-lumen catheter inside the vasculature such that the leading end of the delivery catheter abuts with the proximal end of the multi-lumen catheter, and the multi-lumen catheter and the delivery catheter are displaced together along and guided by the first guidewire and the second guidewire to deliver the medical implant;
positioning the medical implant at a treatment site within the vasculature by adjusting a location of the multi-lumen catheter and the delivery catheter while the multi-lumen catheter and the delivery catheter remain abutted;
releasing the first constraint that maintains at least a proximal portion of the medical implant in a delivery configuration to partially deploy the medical implant; and
releasing the second constraint that maintains at least a middle portion of the medical implant at a diameter that is less than a fully deployed diameter of the medical implant following the release of the first constraint to fully deploy the medical implant.

12. The method of claim 11, wherein the first lumen through which the first guidewire is routed has a first diameter and the second lumen through which the second guidewire is routed has a second diameter different from the first diameter.

13. The method of claim 11, wherein the first lumen through which the first guidewire is routed has a first cross-sectional shape and the second lumen through which the second guidewire is routed has a second cross-sectional shape different from the first cross-sectional shape.

14. The method of claim 11, further comprising routing a third guidewire through a third lumen of the multi-lumen catheter.

15. The method of claim 14, wherein the multi-lumen catheter defines a length, and the first, second, and third lumens extend parallel to one another along the length of the multi-lumen catheter.

16. The method of claim 11, further comprising disposing a multi-lumen catheter olive at the distal end of the multi-lumen catheter through which each of the first and second lumens extends.

17. The method of claim 11, further comprising disposing a plurality of radiopaque markers on the multi-lumen catheter.

18. The method of claim 11, further comprising disposing a delivery catheter olive at the leading end of the delivery catheter and through which the delivery lumen extends.

\* \* \* \* \*